(12) United States Patent
Zhou et al.

(10) Patent No.: US 9,394,259 B2
(45) Date of Patent: Jul. 19, 2016

(54) AUTO-REBOUND SWITCHING APPARATUS AND THE SWITCHING METHOD THEREOF

(75) Inventors: Huasong Zhou, Xiamen (CN); Wei Zhang, Xiamen (CN); Jianmin Chen, Xiamen (CN); Bin Cao, Xiamen (CN)

(73) Assignees: XIAMEN SOLEX HIGH-TECH INDUSTRIES CO., LTD., Xiamen (CN); Huasong Zhou, Xiamen (CN)

( * ) Notice: Subject to any disclaimer, the term of this patent is extended or adjusted under 35 U.S.C. 154(b) by 309 days.

(21) Appl. No.: 14/008,788

(22) PCT Filed: Mar. 30, 2012

(86) PCT No.: PCT/CN2012/073284
§ 371 (c)(1),
(2), (4) Date: Sep. 30, 2013

(87) PCT Pub. No.: WO2012/130155
PCT Pub. Date: Apr. 10, 2012

(65) Prior Publication Data
US 2014/0027234 A1 Jan. 30, 2014

(30) Foreign Application Priority Data
Apr. 1, 2011 (CN) .......................... 2011 1 0082054

(51) Int. Cl.
*C07D 239/47* (2006.01)
*B05B 1/16* (2006.01)
(Continued)

(52) U.S. Cl.
CPC ............ *C07D 239/47* (2013.01); *B05B 1/1636* (2013.01); *B05B 1/18* (2013.01); *C07D 239/48* (2013.01); *C07D 405/12* (2013.01); *C07D 487/04* (2013.01)

(58) Field of Classification Search
CPC ................................ B05B 1/1636; B05B 1/18
USPC .................. 239/393, 396, 443, 444, 446–449
See application file for complete search history.

(56) References Cited

U.S. PATENT DOCUMENTS 3,929,287 A * 12/1975 Givler .................... B05B 1/1663
239/381
4,019,686 A * 4/1977 Palma ...................... B05B 3/021
239/205

(Continued)

FOREIGN PATENT DOCUMENTS

CN         1127679 A      7/1996
CN       101745476 A      6/2010
(Continued)

*Primary Examiner* — Len Tran
*Assistant Examiner* — Alexander Valvis
(74) *Attorney, Agent, or Firm* — Rabin & Berdo, P.C.

(57) ABSTRACT

An auto-rebound switching apparatus has: a body provided with a water-separating apparatus, an upper cover rotatably arranged on the rear side of the body, a passive disc rotatably arranged between the rear side of the body and the upper cover, a clutch mechanism comprising a bi-directional ratchet gear and a bi-directional pawl matching the ratchet gear, the ratchet gear being rotatably arranged on the rear side of the body and transmissively connected to the water-separating apparatus, thus allowing the ratchet gear, when rotating, to drive the water-separating apparatus into motion to allow switching, the bi-directional pawl, the upper cover, and the passive disc being interconnected, allowing the upper cover to rotate relative to the passive disc thus driving the bi-directional pawl to move between a forward rotation position, a reverse rotation position, and a detached position, and a rebound apparatus.

1 Claim, 7 Drawing Sheets

(51) Int. Cl.
   *B05B 1/18* (2006.01)
   *C07D 239/48* (2006.01)
   *C07D 487/04* (2006.01)
   *C07D 405/12* (2006.01)

(56) References Cited

U.S. PATENT DOCUMENTS

| | | | | |
|---|---|---|---|---|
| 4,595,390 | A | * | 6/1986 | Hakim .................. A61F 2/0036 137/530 |
| 5,433,384 | A | * | 7/1995 | Chan ..................... B05B 1/1636 239/239 |
| 2005/0258274 | A1 | * | 11/2005 | Wang .................... B05B 1/1636 239/393 |
| 2011/0000564 | A1 | * | 1/2011 | Corbin ................ F16K 11/0787 137/625.4 |

FOREIGN PATENT DOCUMENTS

| | | |
|---|---|---|
| CN | 101745477 A | 6/2010 |
| CN | 101844117 A | 9/2010 |
| EP | 0742051 A1 | 11/1996 |

\* cited by examiner

AUTO-REBOUND SWITCHING APPARATUS AND THE SWITCHING METHOD THEREOF

FIELD OF THE INVENTION

The present invention relates to an auto-rebound switching apparatus, especially to an auto-rebound switching apparatus applied in a shower.

BACKGROUND OF THE INVENTION

Existing toggle type switching shower usually comprising a shower body, the upper end of the which is disposed with an upper cover, the lower end is disposed with a outlet cover and an outlet mechanism disposed between the outlet cover and the body, the handle of the upper cover near to the body is disposed with a toggle. To switch different outlet functions, it needs to poke the toggle to drive the upper cover to rotate with respect to the body. The upper cover is connected to the outlet mechanism, when the upper cover rotates, the position of the outlet mechanism changes, so that the waterways change, realizing different outlet functions. However, this kind of toggle type switching shower has disadvantages: the upper cover can not rebound, users have to poke the toggle in the opposite direction.

SUMMARY OF THE INVENTION

The object of the present invention is to provide an auto-rebound switching apparatus, which overcomes the technical problem of the existing technology.

The technical proposal of the present invention is as below:

An auto-rebound switching device, wherein comprising:

a body, which is disposed with a water separating apparatus, switching is implemented by the relative motion of the water separating apparatus and the body;

an upper cover, which is rotatably disposed in the rear side of the body;

a passive disc, which is rotatably disposed between the rear side of the body and the upper cover;

a clutch mechanism, which is disposed with a bi-directional ratchet gear and a bi-directional pawl coupled to the ratchet gear; the ratchet gear is rotatably disposed in the rear side of the body, and is connected to drive the water separating apparatus, so that the ratchet gear, when rotating, drives the water separating apparatus to move to implement a switch; the bi-directional pawl, the upper cover and the passive disc are interconnected, so that the upper cover, when rotating with respect to the passive disc, drives the bi-directional pawl to move between a forward rotation position, a reverse rotation position, and a detached position; when the bi-directional pawl is situated in the forward rotation position, the upper cover, when rotating forward, drives the passive disc, the bi-directional pawl and the ratchet gear to rotate forward, when the bi-directional pawl is situated in the reverse rotation position, the upper cover, when rotating reversely, drives the passive disc, the bi-directional pawl and the ratchet gear to rotate reversely; and a rebound apparatus, which is capable to make the bi-directional pawl to situate in detached position and to make the upper cover, the passive disc and the bi-directional pawl rebounded.

In another preferred embodiment, the upper cover is disposed with a protruding toggle.

In another preferred embodiment, the bi-directional pawl is pivot joint to the off-central position of the passive disc, the axis of the passive disc coincides to the axis of the upper cover.

In another preferred embodiment, the body comprising a handle and a disc body, the central of the disc body is disposed with a first circular through hole, an annular groove is disposed in the rear side of the disc body centered on the first circular through hole; the central of the upper cover is disposed with a fourth circular through hole corresponding to the first circular through hole of the body, the front side of the upper cover is disposed with a round of flange coupled to the annular groove of the body, the edge in the rear side of the upper cover is disposed with a toggle, the front side of the upper cover near to the toggle is disposed with a long groove, a limiting block radially extended is disposed between the long groove and the first circular through hole.

In another preferred embodiment, the central of the passive disc is disposed with a second circular through hole, the rear side of the passive disc near the edge is disposed with two radial limiting plates, the limiting block in the front side of the upper cover is locked between the two radial limiting plates of the passive disc, in the edge of the front side, a first pin is further disposed corresponding to and between the two radial limiting plates of the passive disc.

In another preferred embodiment, the bi-directional pawl is a triangle shape, the central is disposed with a third circular through hole, the first pin of the passive disc is inserted into the third circular through hole of the bi-directional pawl; the rear side of one angle near to the outside of the bi-directional pawl is disposed with a second pin, the second pin of the bi-directional pawl is pivot joint to the long groove of the upper cover; the other two angles are respectively disposed with ratchet pawls, a demising groove is disposed between the two ratchet pawls.

In another preferred embodiment, the rebound apparatus comprising at least one spring disposed in one of the body and the passive disc, and a pressing rib disposed in the other of the body and the passive disc, when rotating, the passing rib presses the spring.

In another preferred embodiment, two arc grooves arranged in a circumference direction are disposed to assemble the spring between the annular groove and the first circular through hole of the body, the end of each arc groove close to each other is en-closed, while the other end is respectively disposed with a mouth; in the edge of the front side of the passive disc, two pressing ribs arranged in a circumference direction is disposed, when rotating, the pressing ribs press the spring, the pressing ribs are disposed symmetrically along the diameter; each pressing rib comprising a radial limiting block and an arc protruding rib, two protruding ribs are capable to insert into the arc grooves to press the spring respectively from the mouth of the two arc grooves of the body in a circumference direction.

In another preferred embodiment, it further comprising an apparatus to generate gear affect when the upper cover is rotated.

When using above apparatus, swing the toggle of the upper cover, as the upper cover and the passive disc are interconnected to rotate, the upper cover drives the passive disc to rotate, the passive disc drives the touch apparatus, that is the bi-directional pawl, to rotate, the bi-directional pawl drives the ratchet gear to rotate, the ratchet gear then drives the water separating apparatus in the other side of the body to rotate to implement the switching of the outlet functions. There is further disposed with a rebound apparatus between the body and the passive disc used to rebound the rotation of the upper cover with respect to the body. Under the work of the rebound apparatus, the passive disc is rebounded to drive the upper cover to rebound.

As we can know from above, the present invention is provided with an auto-rebound switching apparatus, which is capable in the sanitary ware, especially in a shower. The advantages of the present invention are: manual toggling of a toggle is required only once, when water spray switching is completed, the rebound apparatus drives the passive disc and the upper cover to rebound, reducing one operation for the user, thus allowing for convenient operation. Also, the apparatus is capable of switching and rebound in both clockwise and counter-clockwise rotations, thus allowing convenient usage.

DETAILED DESCRIPTION OF THE EMBODIMENTS

Figure 1:
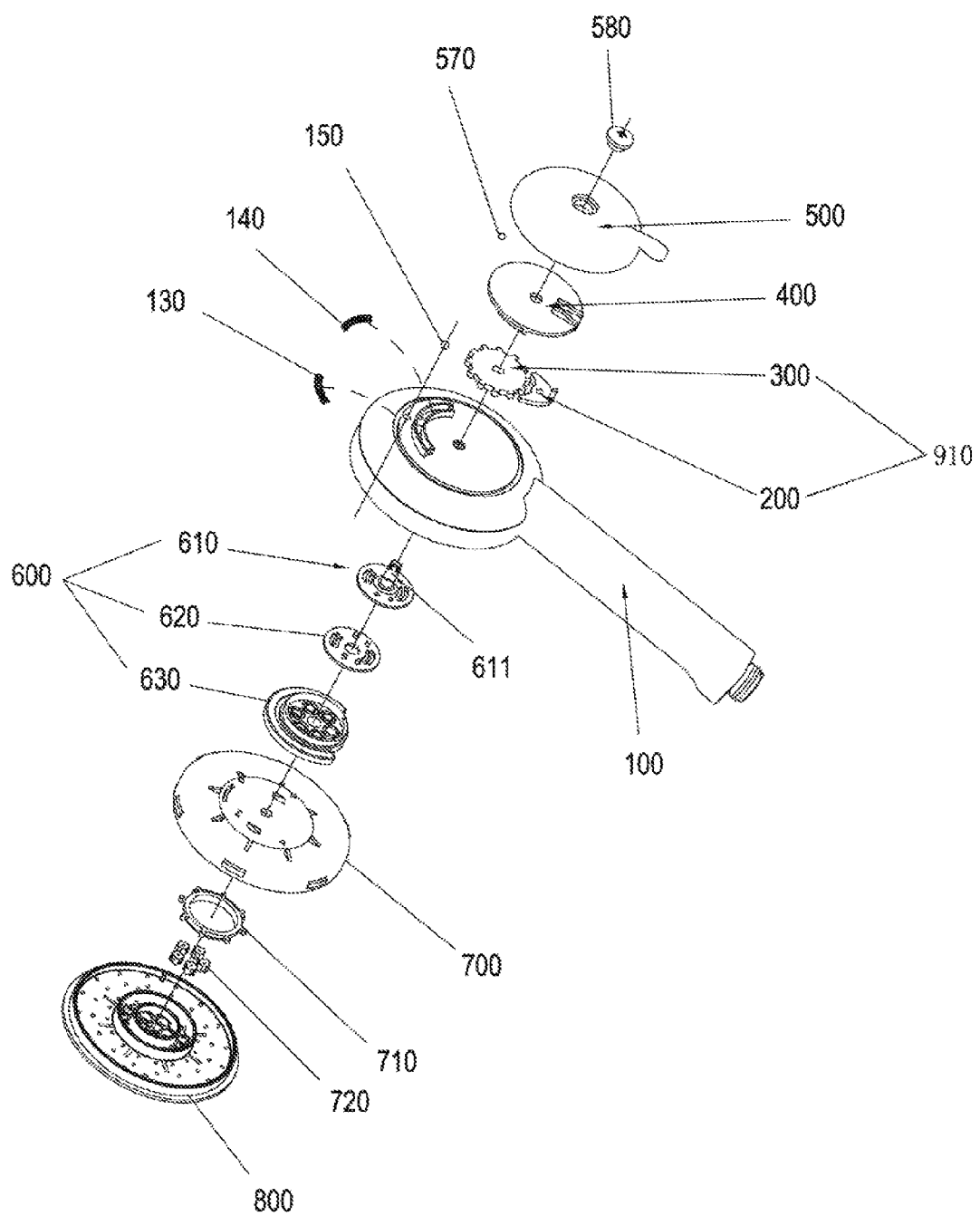
FIG. 1 illustrates the breakdown structure of an auto-rebound switching apparatus of the present invention.
Figure 2:
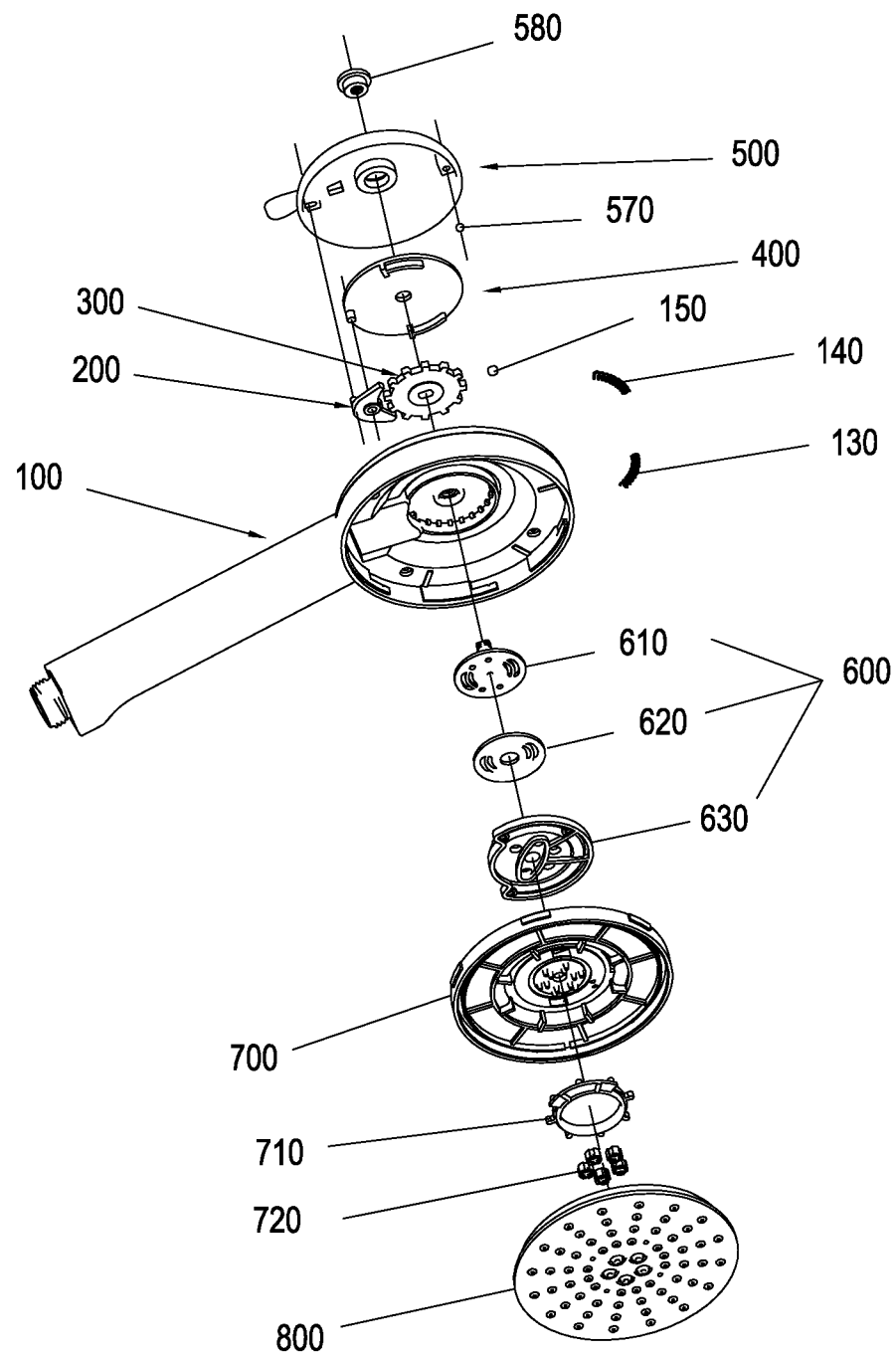
FIG. 2 illustrates the breakdown structure of an auto-rebound switching apparatus of the present invention in another view angle.
Figure 3:
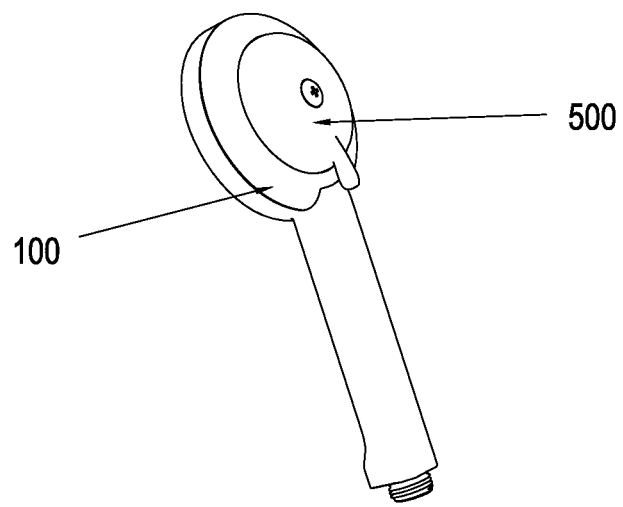
FIG. 3 illustrates the structure of an auto-rebound switching apparatus of the present invention.
Figure 4:
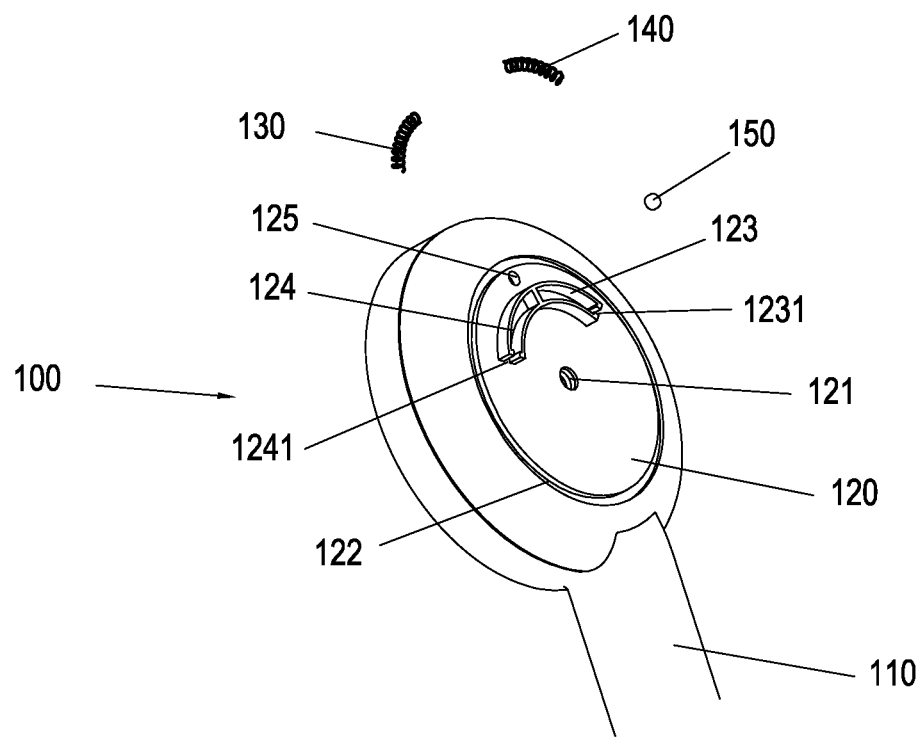
FIG. 4 illustrates the structure of the body.
Figure 5:
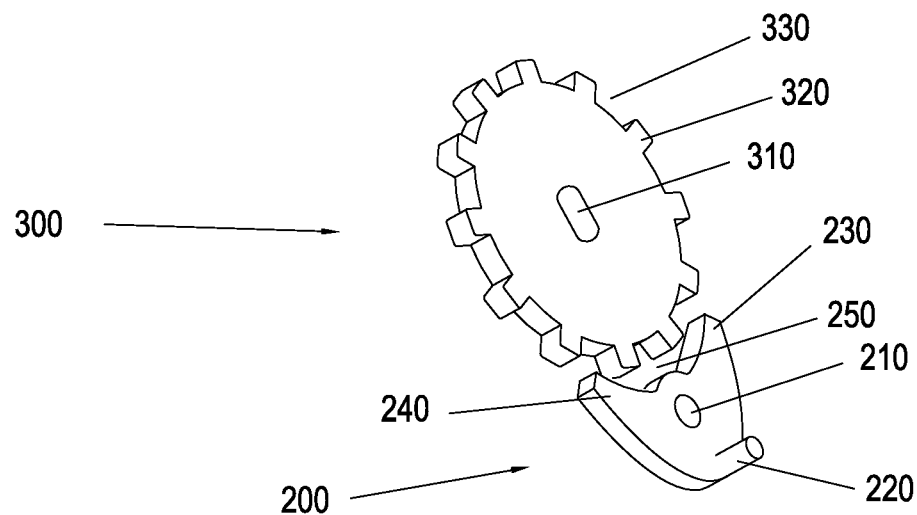
FIG. 5 illustrates the structure of the ratchet gear and the bi-directional pawl.
Figure 6:
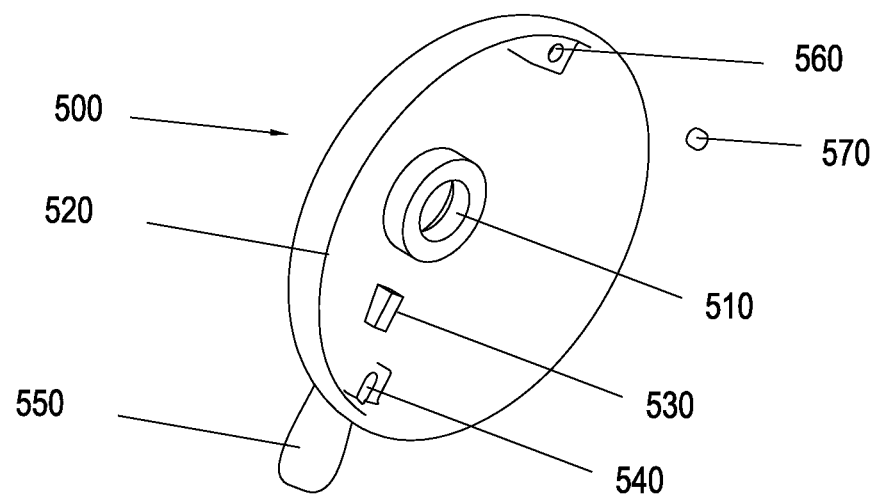
FIG. 6 illustrates the structure of the upper cover.
Figure 7:
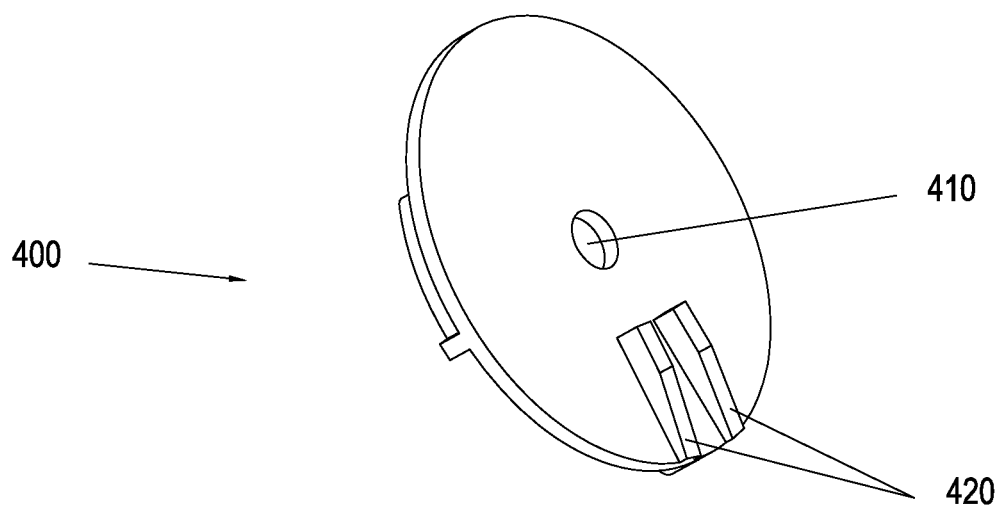
FIG. 7 illustrates the structure of the passive disc.
Figure 8:
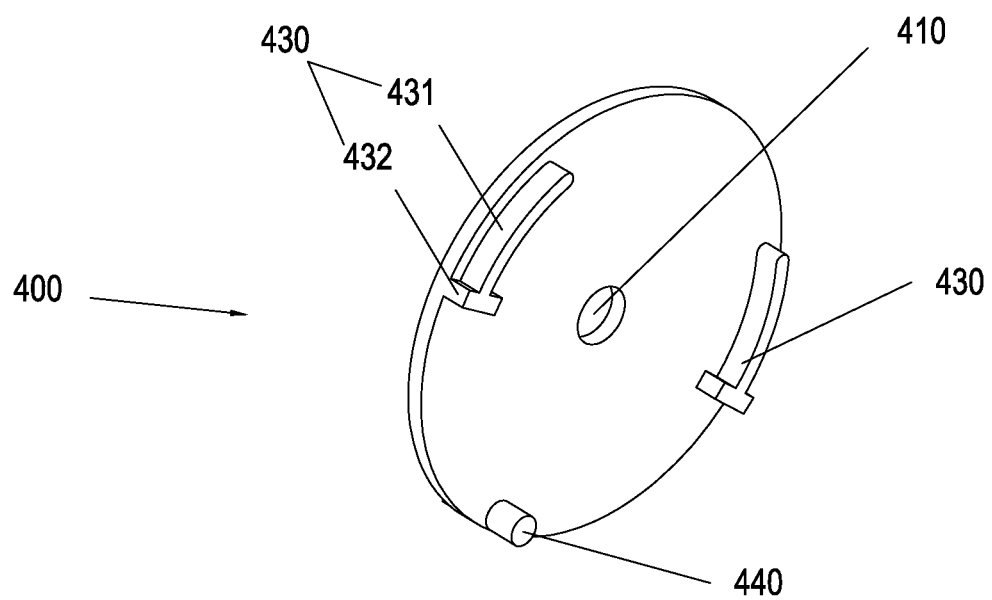
FIG. 8 illustrates the structure of the passive disc in another view angle.

A preferred embodiment of the present invention, refer to FIG. 1 to FIG. 8, is provided with an auto-rebound switching mechanism, which comprising a body 100, a bi-directional pawl 200, a ratchet gear 300, a passive disc 400 and an upper cover 500.

The body 100 includes a handle 110 and a disc body 120, the central position of the disc body is disposed with a first circular through hole 121, an annular groove 122 is disposed in the rear side of the disc body around the first circular through hole 121; between the annular groove 122 and the first circular through hole 121 and in the side opposite to the handle 110, two arc grooves 123 and 124 are symmetrically disposed to assemble two springs 130 and 140, the end of each arc groove close to each other is enclosed, while the other end is respectively disposed with a mouth 1231 and 1241. A first blind hole 125 is further disposed between the arc grooves 123, 124 and the annular groove 122, the first blind hole 125 is disposed with a first magnet 150.

The upper cover 500 covers the rear side of the body 100, the center of the upper cover 500 is disposed with a fourth circular through hole 510 corresponding to the first circular through hole 121 of the body 100, the rear side of the fourth annular through hole 510 is assembled with a screw cap 580. The front side of the upper cover 500 is disposed with a round of a flange 520 corresponding to the annular groove 122 of the body 100, so that the upper cover 500 can rotates about the body 100. The edge of the rear side of the upper cover is disposed with a toggle 550, the front side near to the toggle 550 is disposed with a long groove 540, a limiting block 530 extended in the radial direction is disposed between the long groove 540 and the fourth circular through hole 510. The other side in the front side of the upper cover with respect to the toggle 550 is disposed with a second blind hole 560, a second magnet 570 is disposed inside the second blind hole 560. The first magnet 150 and the second magnet 570 are cooperated to generate gear effect when separated or rebounded A passive disc 400 is disposed between the upper cover 500 and the body 100, the central of the passive disc 400 is disposed with a second circular through hole 410, in the rear side of the passive disc 400 near to the edge is radially disposed with two radial limiting plates 420, the limiting block 530 in the front side of the upper cover 500 is locked between the two radial limiting plates 420. In the edge of the front side of the passive disc 400, a first pin 440 is further disposed corresponding to the two radial limiting plates 420 in the rear side of the passive disc 400; two pressing ribs 430 are disposed in the circumference direction in the edge of the front side, the two pressing ribs 430 are symmetrically disposed, the symmetric line is the diameter of the second circular through hole 410 and the first pin 440. Each pressing rib 430 comprising a radial limiting block 432 and an arc protruding rib 431. The arc core of the protruding rib 431 is the circular through hole 410, and the position of the protruding rib 431 is corresponding to the two arc grooves 123 and 124 of the body 100, the two protruding ribs 431 are rotatably inserted into the arc grooves 123 and 124 from the mouths 1231 and 1241 of the arc grooves 123 and 124 in the circumference direction.

The ratchet gear 300 is disposed between the passive disc 400 and the body 100, the central of the ratchet gear 300 is disposed with a long through hole 310, when assembling, the position of the long through hole 310 is corresponding to the first circular through hole 121 of the body 100. the periphery of the ratchet gear 300 is disposed with several ratchet pawls 320, a clearance 330 is formed between each two adjacent ratchet pawls 320.

The bi-directional pawl 200 is disposed in the side of the ratchet gear 300 between the passive gear 400 and the body 100. It is a triangle shape, the central is disposed with a third circular through hole 210, when assembling, the first pin 440 of the passive disc 400 is inserted into the third circular through hole 210. An angle in the rear side near the outer is disposed with a second pin 220, when assembling, the second pin 220 is inserted into the long groove 540 of the upper cover 500. The other two angles are separately disposed with a pawl 230 and 240, a demising groove 250 is disposed between the two pawls 230 and 240. The pawls 230 and 240 can insert into the clearance 330 of the ratchet gear 300 to poke the ratchet pawls 320.

In the front side of the body 100, it is assembly in order with a water separating apparatus 600, an inclined body 700, a rotor 710, a diverter 720 and a cover 800. thereinto, the water separating apparatus 600 comprising an upper water separating disc 610, a lower water separating disc 620 fixed to the upper water separating disc 610 and a water separating body 630, the central of the upper water separating disc 610 is disposed with a third pin 611 coupled to the long through hole 310 of the ratchet gear 300. When assembling, the third pin 611 is passing through the first circular through hole 121 of the body 100 and then is inserted into the long through hole 310 of the ratchet gear 300.

Figure 9:
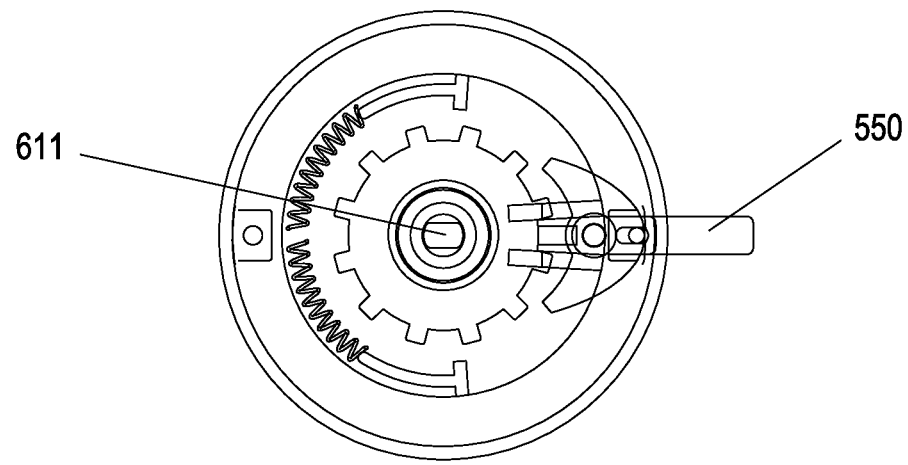
FIG. 9 illustrates the first working state of the present invention.
Figure 10:
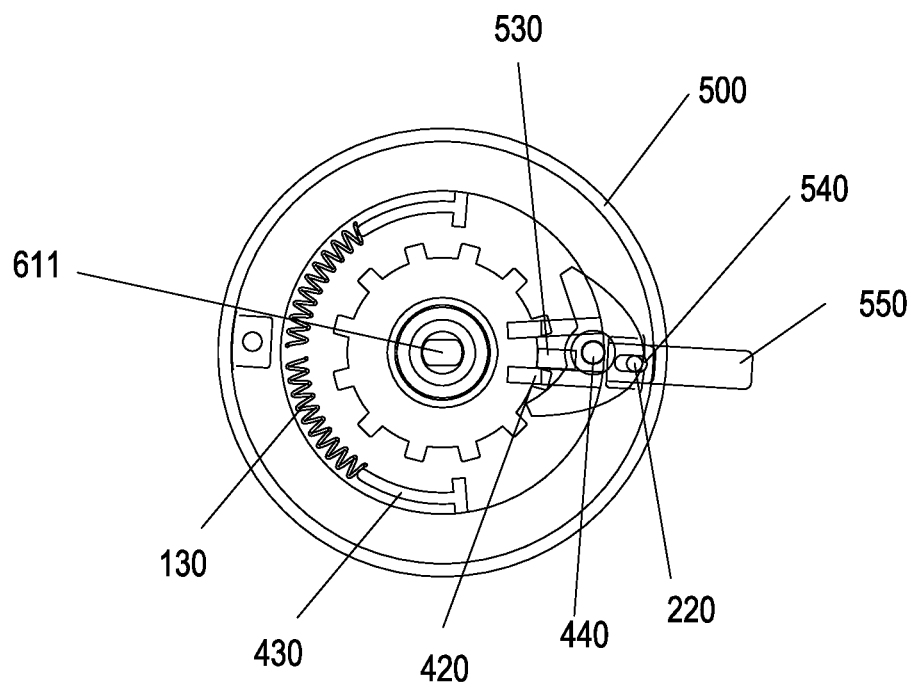
FIG. 10 illustrates the second working state of the present invention.

Please refer to FIG. 9 to FIG. 12 of the working process of the present invention. FIG. 9 is the initial state of the shower. Please refer to FIG. 10, rotate the toggle of the upper cover 500, with the interaction of the groove 540 of the upper cover 500 and the second pin 220 of the bi-directional pawl 200, the bi-directional pawl 200 rotates in a clockwise direction about the first pin 440 of the passive disc 400, and then it is inserted into the ratchet gear, meanwhile the bi-directional pawl is situated in a positive rotation position (correspondingly, when the bi-directional pawl is rotates in opposite direction, it is situated in a negative position). And the limiting block 530 of the upper cover is contacted to the radial limiting plates 420 of the passive disc 400.

Figure 11:
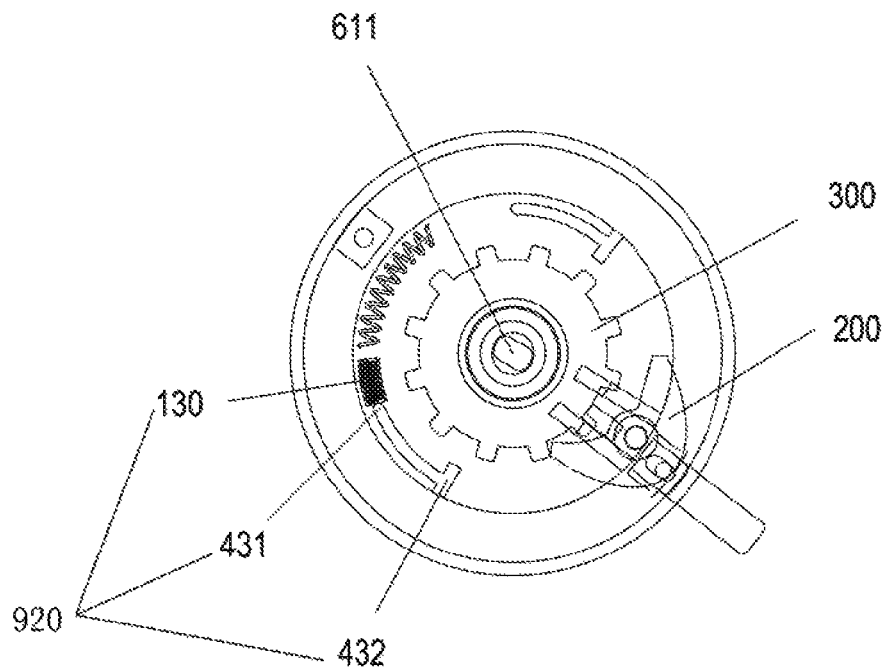
FIG. 11 illustrates the third working state of the present invention.

Refer to FIG. 11, the upper cover 500 drives the passive disc 400 and the bi-directional pawl 200 to rotate in a clockwise direction, the bi-directional pawl 200 drives the ratchet gear 300, the ratchet gear 300 drives the upper water separating disc 610 and the lower water separating disc 620 to rotate in a clockwise direction to realize outlet functions switch. During the process, the protruding rib 431 of the passive disc 400 presses the spring 130, after rotated a certain angle, the radial limiting block 432 in the end of the protruding rib 431 is withstood the arc groove 124 in the rear side of the body, an angle switching is completed.

Figure 12:
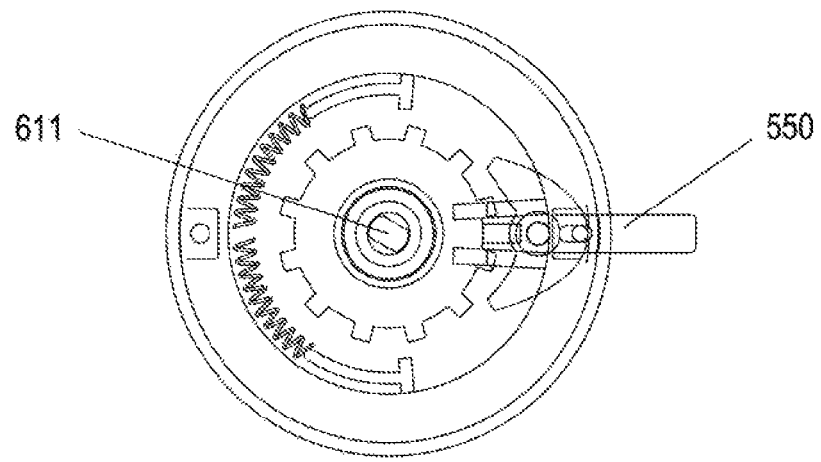
FIG. 12 illustrates the fourth working state of the present invention.

Refer to FIG. 12. the passive disc 400 rotates in a counter-clockwise direction under the pressing of the spring, the passive disc 400 drives the upper cover and the bi-directional pawl to rotate, under the work of the demising groove 250, the bi-directional pawl 200 is separated from the ratchet gear 300, that is the separating position, to rebound with the upper cover, meanwhile the shower is rebounded to the initial state. But the upper water separating body and the lower water separating body have rotated an angle to situate in another outlet function state.

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

INDUSTRIAL APPLICABILITY

The present invention is provided with an auto-rebound switching apparatus, in which manual toggling of a toggle is required only once, when water spray switching is completed, the rebound apparatus drives the passive disc and the upper cover to rebound, reducing one operation for the user, thus allowing for convenient operation. Also, the apparatus is capable of switching and rebound in both clockwise and counter-clockwise rotations, thus allowing convenient usage.

The invention claimed is:

1. An auto-rebound switching device, comprising:
a body, which is disposed with a water separating apparatus, switching is implemented by the relative motion of the water separating apparatus and the body;
an upper cover, which is rotatably disposed in a rear side of the body;
a passive disc, which is rotatably disposed between the rear side of the body and the upper cover;
a clutch mechanism, which is disposed with a bi-directional ratchet gear and
a bi-directional pawl coupled to the ratchet gear;
the bi-directional ratchet gear is rotatably disposed in the rear side of the body, and is connected to drive the water separating apparatus, so that the ratchet gear, when rotating, drives the water separating apparatus to move to implement a switch;
the bi-directional pawl, the upper cover and the passive disc are interconnected, so that the upper cover, when rotated with respect to the passive disc, drives the bi-directional pawl to move between a forward rotation position, a reverse rotation position, and a detached position;
when the bi-directional pawl is situated in the forward rotation position, the upper cover, when rotating forward, drives the passive disc, the bi-directional pawl and the ratchet gear to rotate forward,
when the bi-directional pawl is situated in the reverse rotation position, the upper cover, when rotating reversely, drives the passive disc, the bi-directional pawl and the ratchet gear to rotate reversely; and
a rebound apparatus, which is configured to return the bi-directional pawl to a detached position and to make the upper cover, the passive disc and the bi-directional pawl rebound,
the rebound apparatus further including:
at least one spring disposed in one of the body and the passive disc; and
a pressing rib disposed in the other of the body and the passive disc,
wherein when the upper cover is rotated relative to the passive disc, the passing rib presses the spring;
two arc grooves arranged in a circumference direction are disposed to assemble the spring between an annular groove and a first circular through hole of the body,
each of the two arc grooves having a first end proximate the other arc groove, and a second end opposing the other arc groove,
the first end of each arc groove being enclosed, while the second end is respectively disposed with a mouth;
in an edge of a front side of the passive disc, two pressing ribs arranged in a circumference direction is disposed, when rotating, the pressing ribs press the spring, the pressing ribs are disposed symmetrically along the diameter;
each pressing rib comprising a radial limiting block and an arc protruding rib, two protruding ribs are capable to insert into the arc grooves to press the spring respectively from the mouth of the two arc grooves of the body in a circumference direction.

* * * * *